(12) United States Patent
Kiselev et al.

(10) Patent No.: US 7,018,614 B2
(45) Date of Patent: Mar. 28, 2006

(54) STABILIZATION OF RADIOPHARMACEUTICALS LABELED WITH 18-F

(75) Inventors: Maxim Y. Kiselev, Sterling, VA (US); Vincent Tadino, Washington, DC (US)

(73) Assignee: Eastern Isotopes, Inc., Sterling, VA (US)

( * ) Notice: Subject to any disclaimer, the term of this patent is extended or adjusted under 35 U.S.C. 154(b) by 0 days.

(21) Appl. No.: 10/865,388

(22) Filed: Jun. 10, 2004

(65) Prior Publication Data

US 2004/0223910 A1    Nov. 11, 2004

Related U.S. Application Data

(63) Continuation of application No. PCT/US02/33616, filed on Nov. 5, 2002.

(51) Int. Cl.
*A61K 51/00* (2006.01)
*A61M 36/14* (2006.01)

(52) U.S. Cl. .................. 424/1.89; 424/1.11; 424/1.65; 424/1.81; 424/1.73

(58) Field of Classification Search ............... 424/1.11, 424/1.65, 1.81, 1.85–1.89, 9.1, 1.73; 536/1.11, 536/4.1, 18.4, 18.5, 18.6
See application file for complete search history.

(56) References Cited

U.S. PATENT DOCUMENTS

| | | | |
|---|---|---|---|
| 3,981,769 A | 9/1976 | Winchell et al. | 176/11 |
| 4,232,000 A | 11/1980 | Fawzi | 424/1 |
| 4,436,717 A | 3/1984 | Shiue et al. | 424/1.1 |
| 4,497,744 A | 2/1985 | Fawzi | 260/429.7 |
| 4,818,468 A | 4/1989 | Jungerman et al. | 376/195 |
| 5,037,602 A | 8/1991 | Dabiri | 376/198 |
| 5,082,980 A | 1/1992 | Berridge | 568/917 |
| 5,223,434 A | 6/1993 | Kanno et al. | 436/56 |
| 5,280,505 A | 1/1994 | Hughey et al. | 376/156 |
| 5,384,113 A | 1/1995 | Deutsch et al. | 424/1.69 |
| 5,425,063 A | 6/1995 | Ferrieri | 376/195 |
| 5,436,325 A | 7/1995 | Johnson et al. | 536/4.1 |
| 5,468,355 A | 11/1995 | Shefer et al. | 204/157.2 |
| 5,482,865 A | 1/1996 | Ferrieri et al. | 436/56 |
| 5,573,747 A | 11/1996 | Lacy | 424/1.65 |
| 5,586,153 A | 12/1996 | Alvord | 376/196 |
| 5,759,513 A | 6/1998 | Nakazawa | 424/1.11 |
| 5,762,907 A | 6/1998 | Simon et al. | 424/1.77 |
| 5,770,030 A | 6/1998 | Hamacher et al. | 205/43 |
| 5,917,874 A | 6/1999 | Schyler et al. | 376/194 |
| 5,932,178 A | 8/1999 | Yamazaki et al. | 422/159 |
| 5,961,955 A | 10/1999 | Shochat et al. | 424/1.69 |
| 6,027,710 A | 2/2000 | Higashi et al. | 424/1.65 |
| 6,066,309 A | 5/2000 | Zamora et al. | 424/1.49 |
| 6,172,207 B1 | 1/2001 | Damhaut et al. | 536/18.4 |
| 6,261,536 B1 | 7/2001 | Zamora et al. | 424/1.49 |
| 6,567,492 B1 | 5/2003 | Kiselev et al. | 376/195 |
| 2001/0043663 A1 | 11/2001 | Ruth et al. | 376/195 |
| 2002/0122768 A1 | 9/2002 | Liu et al. | 424/1.11 |
| 2002/0127181 A1 | 9/2002 | Edwards et al. | 424/1.65 |
| 2002/0187099 A1 | 12/2002 | Manchanda | 424/1.49 |

FOREIGN PATENT DOCUMENTS

| | | |
|---|---|---|
| EP | 0 949 632 A2 | 10/1999 |
| JP | 09 054196 A | 6/1997 |
| WO | WO 01/87235 | * 11/2001 |

OTHER PUBLICATIONS

Fowler et al., "2-Deoxy-2-[18F]Fluoro-D-Glucose for Metabolic Studies: Current Status," Appl. Radiat. Isot. vol. 37, No. 8, pp. 663-668 (1986).

Hamacher et al., "Efficient Stereoscopic Synthesis of No-Carrier-Added 2-[18F]-Fluoro-2-Deoxy-D-Glucose Using Aminopolyether Supported Nucleophilic Substitution," J. Nucl. Med. vol. 27, No. 2, pp. 235-238 (1986).

Coenen et al., "Recommendation for a Practical Production of [2-18F]Fluoro-2-Deoxy-D-Glucose," Appl. Radiat. Isot. vol. 38, No. 8, pp. 605-610 (1987).

Knust et al., "Synthesis of 18F-2-Deoxy-2-Fluoro-D-Glucose and 18F-3-Deoxy-3-Fluoro-D-Glucose with No-Carrier-Added 18F-Fluoride," Journal of Radioanalytical and Nuclear Chemistry, Articles, vol. 132, No. 1, pp. 85-91 (1989).

Hamacher et al., "Computer-aided Synthesis(CAS) of No-carrier-added 2-[18F]-Fluoro-2-Deoxy-D-Glucose: An Efficient Automated System for the Aminopolyether -supported Nucleophilic Fluorination," Appl. Radiat. Isot. vol. 41, No. 1, pp. 49-55 (1990).

Fuchtner et al., "Basic Hydrolysis of 2-[18F]Fluoro-1,3,4, 6-tetra-O-acetyl-D-glucose in the Preparation of 2-[18F] Fluoro-2-deoxy-D-glucose," Appl. Radiat. Isot. vol. 47, No. 1, pp. 61-66 (1996).

Paul et al., "Scintigraphy with [18F]2-Fluoro-2-Deoxy-D-Glucose of Cancer Patients," Nucl. Med. Biol. vol. 13, No. 1, pp. 7-12 (1986).

(Continued)

*Primary Examiner*—Dameron L. Jones
(74) *Attorney, Agent, or Firm*—Mark Douma

(57) ABSTRACT

An $^{18}$F isotope-labeled FDG radiopharmaceutical is stabilized against degradation in radiochemical purity due to radiolysis using selected amounts of ethyl alcohol that depend on the activity concentration of the $^{18}$F with due regard to limits set by various pharmacopoeia standards. Any of the well-know production methods for the FDG may be used and the ethyl alcohol added at several stages, preferably as part of the standard hydrolysis step. This particular radiopharmaceutical is used extensively in diagnostic imaging with a Positron Emission Tomography technique.

16 Claims, No Drawings

OTHER PUBLICATIONS

USP Expert Committee: (RMI) Radiopharmaceuticals and Medical Imaging, "Fludeoxyglucose F 18 Injection," Pharmacopeial Forum, vol. 27, pp. 2145 et seq, date is not available.

L. Lindner et al., "A Dynamic Loop Target for the In-Cyclotron Production of F-18 by the 16O(a,d)16F Reaction on Water," Int. J. Appl. Radiat Isot., vol. 24, pp 124-126 (1973).

R. Iwata et al., "[18F]Fluoride Production with at Circulating [18O]Water Target," Appl. Radiat. Isot., vol. 38, No. 11, pp 979-984 (1987).

H.-J. Helmeke et al., A water target with beam sweep for routine fluorine-18 production, Appl. Radiat. Isot., vol. 54, No. 5, pp. 753-759 (2001).

O. Solin et al., "Production of 18F from Water Targets. Specific Radioactivity and Anionic Contaminants," Appl. Radiat. Isot., vol. 39, No. 10, pp. 1065-1071 (1988).

E. J. Knust et al., "High Yield Production of 18-F in a Water Target via the 16O(3He,p)18F Reaction," Int. J. Appl. Radiat. Isot., vol. 34, No. 12, pp. 1627-1628 (1983).

O. T. DeJesus et al., "[18F]Fluoride from a Small Cyclotron for the Routine Synthesis of [18F]2-Fluoro-2-Deoxy-D-Glucose," Appl. Radiat. Iso., vol. 37, No. 5, pp. 397-401 (1986).

E. J. Knust et al., "Production of Fluorine-18 Using an Automated Water Target and a Method for Fluorination Aliphatic and Aromatic Compounds" Appl. Radiat. Isot.., vol. 37, No. 8, pp. 853-856 (1986).

Jean-Luc Morelle et al., "An Efficient [18F]Fluoride Production Method Using a Recirculating 18O Water Target," Proc. 3rd Workshop on Targetry and Target Chem., Vancouver, B.C., pp. 50-51 (1989) at www.triumf.ca/wttc/pdf/1989/Sec4-4.pdf.

G. K. Mulholland et al., "Reliable Pressurized Water Target for F-18 Production at High Beam Currents," J. Labeled Cmpds. Radiopharm., vol. 26, pp. 192-193 (1989).

M. Sajjad et al., "Cyclotron Targetry for Medical Isotope Production," Nuclear Instruments and Methods in Physics Research, vol. B40/41, pp. 100-1104 (1989).

C. W. Alvord et al., "Target System for the RDS-111 Cyclotron," Proc. 6th Workshop on Targetry and Target Chem., Vancouver, B.C., pp. 155-161 (1995) at www.triumf.ca/wttc/pdf/1995/Sec4-9.pdf.

M. R. Kilbourn et al., "A Simple [18O]Water Target for [18F]Fluoride Production," Int. J. Appl. Radiat. Isot., vol. 35, No. 7, pp. 599-602 (1984).

M. R. Kilbourne et al., "An Improved [18O]Water Target for [18F]Fluoride Production," Int. J. Appl. Radiat. Isot., vol. 36, No. 4, pp. 327-328 (1985).

T. J. Tewson et al., "Routine Production of Reactive Fluorine-18 Fluoride Salts from an Oxygen-18 Water Target," Nuc. Med. Biol., vol. 15, No. 5, pp. 499-504 (1988).

R. D. Hichwa et al., "Design of Target Systems for Production of PET Nuclides," Nuclear Instruments and Methods in Physics Research, vol. B40/41, pp. 1110-1113 (1989).

* cited by examiner

STABILIZATION OF RADIOPHARMACEUTICALS LABELED WITH 18-F

CROSS REFERENCE TO RELATED APPLICATIONS

This application is a continuation of and claims priority from application PCT/US02/33616, filed on 05 Nov. 2002 in the RO/US, incorporated herein by reference.

BACKGROUND

1. Technical Field

This invention relates to stabilization against auto radiolysis of a glucose compound that incorporates an $^{18}$F radioisotope. The stabilized compound is used for diagnostic imaging using Positron Emission Tomography (PET). Related inventions may be found in U.S. main class 424, subclass 1.89.

2. Background

The $^{18}$F isotope-labeled glucose, [$^{18}$F] 2-Fluoro-2-Deoxy-D-glucose (hereinafter FDG), has become widely used in nuclear medicine for diagnostic studies using a Positron Emission Tomography (PET) body scanning technique. Because of the short half-life of the $^{18}$F isotope (109 min), this product must be produced in relatively large quantities to allow for decay during delivery to the patient from a manufacturing facility. Therefore, work shifts usually start near midnight with production for distant (via automobile) hospitals first, followed by that for nearby hospitals in the very early morning. Typical delivery time can be as long as 5–8 hours. After arrival, there could be another 4 hour delay before use on the last patient. Thus, 8–12 hours can pass from the time of production to the time of administration to a patient. This is 4.4–6.6 half-lives and necessitates preparation of initial radioactivity concentrations of 20–100 times greater than is actually required at the time of administration.

(Although not the only method, currently, the preferred method of producing the $^{18}$F isotope is by bombarding water enriched with the $^{18}$O isotope using high energy protons from a cyclotron. Additional information may be found in U.S. Pat. No. 6,567,492, issued May 20, 2003 to Kiselev et al., and the references cited therein.)

If prepared in relatively high concentrations, for example, 3.7 GBq/ml (100 mCi/ml) and higher, radiation-induced decomposition of FDG is observed. This process is referred to as radiolysis. It is caused mainly by oxidation by free radicals that are produced by the interaction of ionizing radiation from the $^{18}$F isotope with the water solvent and possibly air. These processes may then lead to the decomposition of FDG, which can be quantified in terms of decreased Radio Chemical Purity (RCP). RCP is typically expressed as a % of activity in the form of FDG relative to the total radioactivity present in the sample.

At the end of production, FDG typically has an RCP of 98–100%. As a result of radiolysis, some FDG molecules decompose resulting in other than FDG radioactive substances (mainly free 18F$^-$ ions). As demonstrated by experiments described below, this can lead to a decline in RCP to less than 90% over a period of less than 12 hours. The quality standard established by the US Pharmacopoeia (USP) for FDG is "not less than 90% RCP." It is obviously desirable to retain as high an RCP as possible for as long as possible to achieve the best PET image quality.

FDG production comprises synthesis of the $^{18}$F labeled compound followed by purification. Synthesis involves an $^{18}$F fluorination step which leads to formation of an acetylated derivative of FDG (an intermediate product) and then a hydrolysis step during which protective acetyl groups are removed resulting in the final product. The hydrolysis step takes only about 10 minutes, but the concentration of radioactive material is about five times as high as in the final product leading to significant decomposition of the FDG intermediate as it is being produced. Decomposition of the intermediate product will not directly affect the RCP of the final product due to the fact that accumulated radioactive impurities are removed during the purification step. However, it is important to realize that any decomposition will result in a lower radiochemical yield. Therefore, it is very useful to reduce or control radiolysis not only of the final product but also the intermediate product during hydrolysis.

For the purpose of distribution and use, the 12 hour storage capability is a practical requirement. Therefore, RCP after 12 hours or longer is a useful indicator of stabilization effectiveness.

In summary, improving the stability of FDG and increasing the RCP at the time of administration is an important goal for FDG manufacturers. It is also important to control radiolysis during the FDG production steps to increase radiochemical yield of the product.

Production of $^{18}$F-labeled FDG is, by now, well, known. Information can be found in: 1) Fowler et al., 2-Deoxy-2-[18F]Fluoro-D-Glucose for Metabolic Studies: Current Status," Applied Radiation and Isotopes, vol. 37, no. 8, 1986, pages 663–668; 2) Hamacher et al., "Efficient Stereospecific Synthesis of No-Carrier-Added 2-[18F]-Fluoro-2-Deoxy-D-Glucose Using Aminopolyether Supported Nucleophilic Substitution," Journal of Nuclear Medicine, vol. 27, 1986, pages 235–238; 3) Coenen et al., "Recommendation for Practical Production of [2-18F]Fluoro-2-Deoxy-D-Glucose," Applied Radiation and Isotopes, vol. 38, no. 8, 1987, pages 605–610 (a good review); 4) Knust et al., "Synthesis of 18F-2-deoxy-2-fluoro-d-glucose and 18F-3-deoxy-3-fluoro-D-glucose with no-carrier-added 18F-fluoride," Journal of Radioanalytic Nuclear Chemistry, vol. 132, no. 1, 1989, pages 85+; 5) Hamacher et al., "Computer-aided Synthesis (CAS) of No-carrier-added 2-[18F]Fluoro-2-Deoxy-D-Glucose: An Efficient Automated System for the Aminopolyether-supported Nucleophilic Fluorination," Applied Radiation and Isotopes, vol. 41, no. 1, 1990, pages 49–55; and 6) U.S. Pat. No. 5,932,178, issued Aug. 3, 1999 to Yamazaki et al. for "FDG Synthesizer Using Columns."

With respect to stabilization of radiopharmaceuticals, U.S. Pat. No. 5,762,907, issued Jun. 9, 1998 to Simon et al., discloses a freeze/thaw technique to preserve the radiopharmaceutical, ethylenediamine-tetraehtylenephosphonic acid (EDTMP), labelled with, for example, $^{153}$Sm. Radiometric degradation versus time is compared to solutions containing 0.9% benzyl alcohol, 5.0% ethanol, and a no-preservation control. The benzyl alcohol solution delays the start of degradation, after which the rate is moderate. In contrast, even at the high 5.0% concentration, ethanol delays degradation slightly, but then degradation proceeds at an even faster rate than the control. Use of other additives to stabilize various radiopharmaceuticals was discussed in U.S. Pat. No. 5,384,113, issued Jan. 24, 1995 to Deutsch et al.; U.S. Pat. No. 6,027,710, issued Feb. 11, 2000 to Higashi et al.; U.S. Pat. No. 6,066,309, issued May 23, 2000 to Zamara et al.; and U.S. Pat. No. 6,261,536, issued Jul. 17, 2001 to Zamara et al.

Mention can be made of US pre-grant publication 2002/0127181, dated Sep. 12, 2003 and applied for by Edwards et al. This application discusses a very wide range of radiopharmaceuticals useful in producing angiograms. Paragraphs 0238 and 0239 discuss synthesis of FDG labeled with 18-F. The next paragraph lists a number of stabilizers "comprising an effective amount of one or more stabilizers selected from ascorbic acid, benzyl alcohol, gentisic acid or its metal salts, p-aminobenzoic acid or its salt forms, cysteamine, 5-amino-2-hydroxybenzoic acid or its metal salt forms, nicotinic acid or its metal salt, nicotinamide, polyhydroxylated aromatic compounds, aromatic amines, and hydroxylated aromatic amines." But no mention is made of ethanol. Paragraph 0266 lists additional stabilizers as cysteine, monothioglycerol, sodium bisulfite, sodium metabisulfite, and inositol, again without mentioning ethanol. However, the next paragraph states that "Solubilization aids useful in the preparation of radiopharmaceuticals . . . include but are not limited to ethanol (emphasis added), glycerin . . . . Preferred solubilization aids are polyethylene glycol and Pluronics."

Since the PET procedure requires injecting the FDG solution, there is a USP requirement to keep any ingredient with toxic potential within appropriate limits. Currently, the allowed dose of the above cited ethanol in the European Pharmacopoeia and USP is 0.5% (one tenth the concentration used above for EDTMP). Moreover, conformance requires demonstration by one or more validated limit tests. From a practical standpoint, it is very desirable to keep the concentration of any such potentially toxic ingredients at or below one half of the limit value, i.e., 0.25%. Because of assay uncertainty and safety factor considerations, using more than about one half the limit value requires considerably more testing to demonstrate conformance with confidence.

SUMMARY

Accordingly, one objective of the invention is to increase the stability of FDG and hence the RCP of the product at the time of use. An additional objective is to increase process efficiency by controlling radiolysis during FDG production. These need to be accomplished at the same time that potentially toxic additives are kept within practical safe limits.

Surprisingly, these objectives can be realized in an $^{18}$F-labeled FDG in water composition that incorporates ethanol in the final product having a concentration in a range of a minimum effective stabilization amount up to a practical pharmacopoeia limit. A minimum effective concentration is one that maintains a 90% RCP for 12 hours or more. When the $^{18}$F activity concentration is about 10 GBq/ml, it was found experimentally that the minimum effective ethanol concentration is about 0.1% (v/v). Given these experimental results, for a practical range of activity concentrations, it can be shown theoretically that a linear approximation to the minimum effective ethanol concentration is about 0.01% (v/v) per GBq/ml of $^{18}$F activity concentration.

The upper limit on the ethanol concentration is given by various country pharmacopoeia limits. Currently, this is 0.5% (v/v) for ethanol in FDG solutions, but a reduced upper limit of about 0.25% (v/v) is more practical to ensure regulatory compliance. At least for $^{18}$F activity concentrations of about 10 GBq/ml or less, an ethanol concentration in the range of about 0.1% to 0.25% (v/v) is an effective, safe stabilizer of FDG solutions.

When FDG is synthesized using a nucleophilic $^{18}$F fluorination step followed by a hydrolysis step, as described in more detail below, ethanol may be added either to the NaOH hydrolyzing reagent solution, the dilution water, the collection vial, an NaCl solution added to the collection vial, or to a combination of these. When added to the NaOH solution, the stabilizing effect is achieved as early as possible in the process. No matter when it is added, the amount of ethanol should be adjusted to produce the concentrations in the final product described above.

DETAILED DESCRIPTION

The FDG production process described herein is based on an automated FDG synthesizer supplied by Nuclear Interface GmbH (Muenster, Germany). The description of the system and radiochemical synthesis is provided as an illustration only. Many suitable types of apparatus and processes are used to synthesize FDG and have been well know for some time. Synthesis of the FDG itself is not considered to be part of this invention and only a basic description of a process is included here.

The synthesizer system includes a synthesis module control unit, chemical process control unit and a computer. The control unit is located inside a lead shielded enclosure and contains a number of reagent tubes, vials, and valves; a reaction and a product collection vessel; and connections for purification columns and cartridges.

The usual synthesis of FDG is a two-step process consisting of two chemical reactions: a nucleophilic $^{18}$F fluorination followed by a hydrolysis step.

The fluorination step incorporates an $^{18}$F label into an organic precursor, 1,3,4,6-tetra-O-acetyl-2-O-trifluoromethanesulfonyl-β-D-mannopyranose (mannose triflate). The substitution reaction is accomplished by combining a phase transfer catalyst, with $^{18}$F fluoride extracted from an irradiated target material. The mixture is dried out in a stream of inert gas. This dried mixture is added to a solution of the mannose triflate in acetonitrile and this solution is heated and dried in a stream of inert gas.

The hydrolysis step, as exemplified by a base-catalyzed hydrolysis of the acetyl protecting groups, generates the free hydroxyl groups of the final drug product. A predetermined amount of solution of NaOH in water is added as a hydrolyzing reagent to the dry fluorinated mannose triflate and the resulting solution is heated to achieve complete removal of acetyl groups.

To purify the resulting mixture and leave a solution of FDG in water, it is diluted in a predetermined amount of water and filtered through purification cartridges.

This invention is not dependant on the details of the above steps and should apply to any process that uses a nucleophilic fluorination step followed by a hydrolysis step. Moreover, in the future, some other process may be developed that does not use the two step process just described. In that case, most likely, the invention could be adapted to that process as well without undue experimentation.

Four Working Examples:

To examine the affect of the addition of ethyl alcohol on the stability of FDG in a water solution, it was produced as described above. Each run produced between 82 and 106 Bq (2.3–2.8 Ci) of FDG in 9 ml of water. Thus, the initial activity concentration, just after the end of production, ranged from about 8–11 GBq/ml (263–320 mCi/ml).

In all experiments, the RCP was determined using a standard Thin Layer Chromatography (TLC) method using 10 cm silica-coated glass plates supplied by Alltech (Deerfield, Ill.). A 95:5 mixture of acetonitrile and water was used as a mobile phase and a TLC plate scanner supplied by Bioscan (Washington, D.C.) was used to measure the radioactivity distribution on the plate. In most cases, the sample size was less than 1 μl.

Ethanol concentrations were determined with Gas Chromatograph (GC) analysis using an HP 5890 gas chromatograph equipped with 50 m capillary column, type DB WAX, supplied by Alltech and a standard HP flame ionization detector (FID). The carrier gas was helium at 4–10 ml/min. The FID injector was split 1:50 and heated at 200° C. The column temperature was 50–200° C. with a 20° C./min. ramp. The FID detector response was calibrated using an external standard.

RCP was measured after storage times that ranged from 14 to 21 hours. It should be noted, however, that most of the radiolysis takes place in the first 3–6 hours due to the fact that the radioactivity concentration decreases exponentially over time with a half-life of 1.82 hours. After 6 hours, only about 10% of the radioactivity remains and is probably not sufficient to cause any significant decomposition of the product.

Experiment 1: Ethanol Added to the Final FDG Product.

In this experiment, the final product was prepared with an initial activity concentration of 10.8 GBq/ml (292 mCi/ml). The product was split into 4 equal portions of 2 ml each and labeled as samples 1, 2, 3, and 4 to which ethanol was added in varying amounts using a micro-syringe. Samples were kept in tightly sealed vials identical to those used for storage and delivery of FDG to customers. The RCP was measured at the time of production and after 14 hours. Ethanol concentrations in each of the samples were also measured using the GC method described above. The Table 1 shows the results.

TABLE 1

| Sample# | Ethanol (%) | Initial RCP | 14 hour RCP |
|---|---|---|---|
| 1 | 0.05% | 97.2% | 87% |
| 2 | 0.24% | " | 97% |
| 3 | 0.48% | " | 96% |
| 4 | 1.07% | " | 97% |

As Table 1 show, 0.05% is not a high enough concentration to maintain an RCP that meets USP requirements but, within experimental error, concentrations of 0.24% or more suffered negligible degradation in RCP. Of course, 1.07% exceeds pharmacopoeia limits and 0.48% may be too close.

Experiment 2: Ethanol Added to the NaOH Solution.

In this experiment, to simplify the manufacturing process and provide an added benefit of stabilizing the intermediate product, ethanol was added to the NaOH hydrolyzing reagent solution that was used in the hydrolysis step. It was added in an amount calculated to result, after dilution with water, in about a 0.05% concentration in the final product. In this experiment, the final product had an initial activity concentration of about 11.8 GBq/ml (320 mCi/ml).

Samples 1, 2, and 3, each of 2 ml, were taken from the final product. To see if storage conditions affected the results, samples 1 and 2 were stored in vials while sample 3 was stored in a syringe identical to those that are used to deliver FDG to users. Each sample was analyzed at the end of a 15 hour waiting period using the TLC and GC methods described above. Table 2 shows the results.

TABLE 2

| Sample# | Ethanol (%) | Initial RCP | 14 hour RCP |
|---|---|---|---|
| 1 | 0.04% | 98.9% | 89.7% |
| 2 | 0.04% | " | 89.8% |
| 3 | 0.05% | " | 87.8% |

The results indicate that, even when added to the NaOH solution, an ethanol concentration of 0.04%–0.05% is not enough. There was still enough loss of RCP so that the product fails the USP limit of 90% RCP at the end of the storage period. Syringe storage appeared to be the worst, but is probably within experimental error.

Experiment 3: Increased Ethanol Added to the NaOH Solution:

These experiments were identical to Experiment 2 except that ethanol added to the NaOH solution was doubled resulting in an approximately 0.1% ethanol concentration in the final product. Two different activity concentrations and storage times were tried. For each, samples 1 and 2 were stored in vials, while samples 3 and 4 were stored in syringes.

Table 3 shows the results for an initial activity concentration of 9.7 GBq/ml (263 mCi/ml) after 21 hours.

TABLE 3

| Sample# | Ethanol (%) | Initial RCP | 21 hour RCP |
|---|---|---|---|
| 1 | 0.09% | 99.5% | 94.4% |
| 2 | 0.09% | " | 94.7% |
| 3 | 0.11% | " | 95.6% |
| 4 | 0.11% | " | 95.2% |

Table 4 shows the results for an initial activity concentration of 11.2 GBq/ml (303 mCi/ml) after 15 hours.

TABLE 4

| Sample# | Ethanol (%) | Initial RCP | 15 hour RCP |
|---|---|---|---|
| 1 | 0.08% | 98% | 94.6% |
| 2 | 0.09% | " | 94.2% |
| 3 | 0.10% | " | 94.5% |
| 4 | 0.11% | " | 95.1% |

Although there is still an appreciable loss of RCP, all samples met the USP limit of 90% RCP at the end of the 15 & 21 hour storage period. The stabilizing effect of a 0.1% ethanol concentration is therefore sufficient at FDG activity concentrations at least up to 11.2 GBq/ml (303 mCi/ml). An ethanol concentration of 0.1% is well below the 0.5% limit admitted by European Pharmacopoeia and USP.

As expected, due to the reduced $^{18}$F decay and reduction in activity, the loss of RCP after 21 hours is not significantly worse than after 15 hours. Storage method made little difference in the RCP.

In summary, for FDG solutions with an activity concentration of about 10 GBq/ml, an ethanol concentration of at least about 0.1% (v/v) is an effective concentration to stabilize the solution against radiolysis to yield a 90% RCP after 12 hours. While the pharmacopoeia limits are higher than this, as a general rule, using the lowest concentration of additives to a pharmaceutical is always desirable. As noted above, lesser amounts help ensure that limits are not exceeded.

Therefore, for other activity concentrations, it would be useful to know the minimum effective amount. Based on the experimental results described above that showed that a 0.1% ethanol concentration is effective for an activity concentration of 10 GBq/ml, it should take only moderate effort for one skilled in the art to prepare different practical activity concentrations of FDG and determine the required ethanol concentrations.

The effort can be considerably reduced, however, if one uses a concentration of ethanol that is linearly proportional to the activity, i.e., 0.01% (v/v) per GBq/ml. This is because the densities of both $^{18}$F-labeled FDG and ethanol molecules are low. There should be little interaction between the molecules of each of these species with themselves in the water solution. For 10 GBq/ml, the density is about $10^{14}$ FDG molecules/cc so that there is about 20,000 nm between them. For 0.1% ethanol, the density is about $1.3 \times 10^{19}$ molecules/cc, a spacing of about 500 nm in a water solution having a density of about $3 \times 10^{22}$ molecules/cc with an inter-molecular spacing of about 0.3 nm.

It is thought that the $^{18}$F positron emission produces a cascade of free radical species including O*, OH*, and others that react with the FDG, unless intercepted by ethanol molecules. Whether true or not, it is clear that the major positron interaction is with water molecules. This should be a liner function of the number of $^{18}$F emitters in solution. Assuming the ethanol has a protective effect, the amount required should be linearly related to the number of free radicals and thus the $^{18}$F density.

While experimental confirmation is always desirable when dealing with injected radiopharmaceuticals, the linear approximation to the least effective ethanol concentration should be reasonably close, at least up to the pharmacopoeia limits of 0.5% ethanol.

Even though a finite set of examples of the invention have been provided, it should be understood that the scope of the claims are not thereby limited but encompass equivalent variations. All patents and publications are incorporated herein by reference as though done individually.

What is claimed is:

1. A radiopharmaceutical composition comprising:
   $^{18}$F isotope-labeled FDG in water having an activity concentration; and
   ethanol with a final product concentration having a minimum of 0.1% (v/v).

2. The composition according to claim 1 wherein the minimum ethanol concentration is at least about 0.01% (v/v) per GBq/ml of $^{18}$F activity concentration.

3. The composition according to claim 1 wherein the ethanol concentration is about 0.1% (v/v) for a 10 GBq/ml $^{18}$F activity concentration.

4. The composition according to claim 1 wherein the ethanol concentration is in the range of about 0.1% (v/v) to 0.5% (v/v).

5. The composition according to claim 1 wherein the ethanol concentration is in the range of about 0.1% to 0.25% (v/v).

6. A process for preparing an $^{18}$F isotope-labeled FDG radiopharmaceutical composition in water comprising a nucleophilic $^{18}$F fluorination step followed by a hydrolysis step and the step of adding ethanol with a minimum concentration of about 0.1% (v/v) in the final product.

7. The process according to claim 6 wherein the minimum ethanol concentration is at least about 0.01% (v/v) per GBq/ml of $^{18}$F activity concentration.

8. The according to claim 6 wherein the ethanol concentration is about 0.1% for a 10 GBq/ml $^{18}$F activity concentration.

9. The process according to claim 6 wherein the ethanol concentration is in the range of about 0.1% (v/v) to 0.5% (v/v).

10. The process according to claim 6 wherein the ethanol concentration is in the range of about 0.1% to 0.25% (v/v).

11. The process according to claim 6 wherein the ethanol is added to a hydrolyzing reagent used during the hydrolysis step.

12. The composition according to claim 11 wherein the minimum ethanol concentration is at least about 0.01% (v/v) per GBq/ml of $^{18}$F activity concentration.

13. The composition according to claim 11 wherein the ethanol concentration is about 0.1% for a 10 GBq/ml of $^{18}$F activity concentration.

14. The composition according to claim 11 wherein the minimum ethanol concentration is about 0.1% (v/v).

15. The composition according to claim 11 wherein the ethanol concentration is in the range of about 0.1% (v/v) to 0.5% (v/v).

16. The composition according to claim 11 wherein the ethanol concentration is in the range of about 0.1% to 0.25% (v/v).

* * * * *